Nov. 5, 1935. L. C. BOBBINK Plant Pat. 147
AZALEA
Filed June 1, 1935
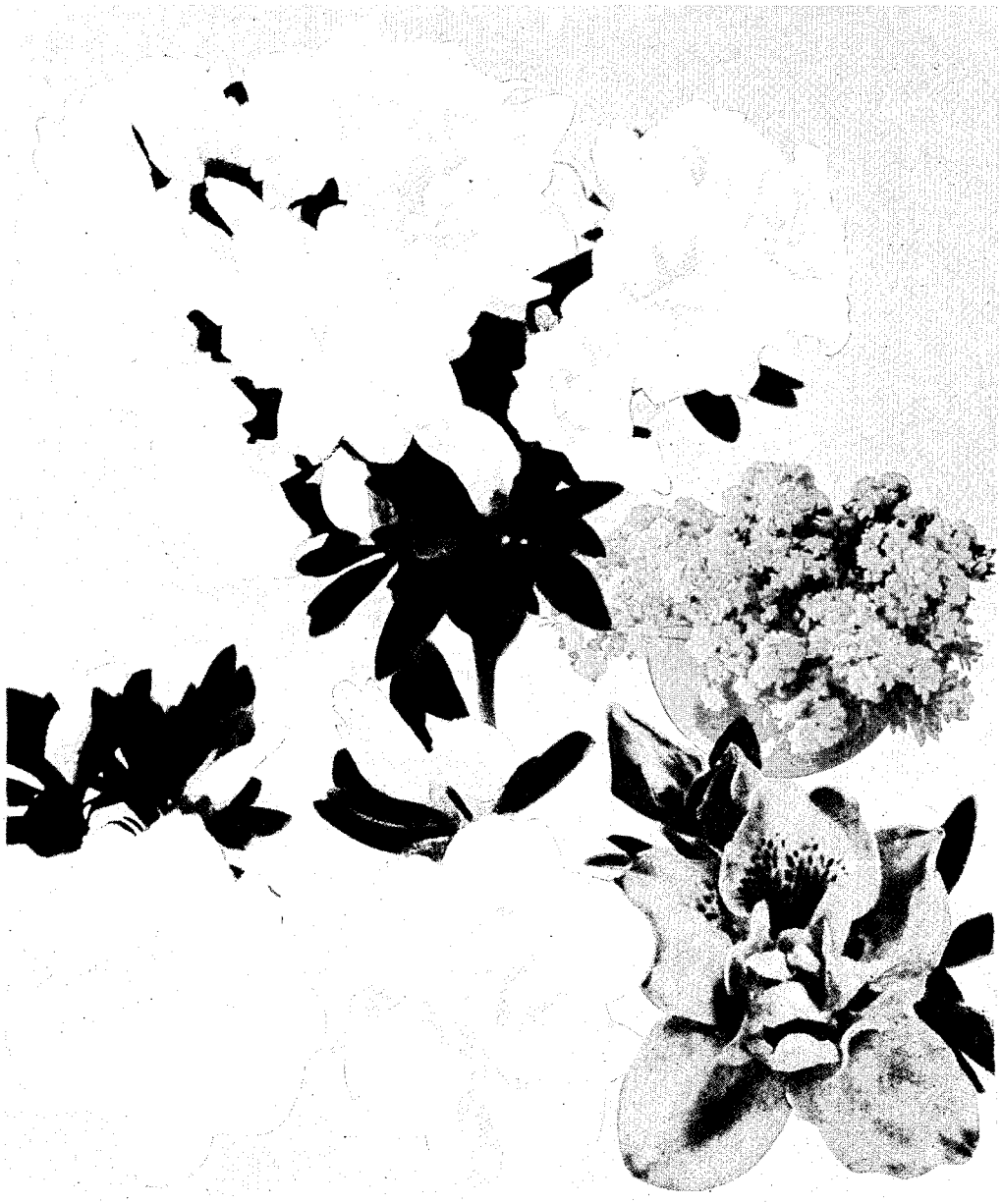
INVENTOR
Lambertus Christian Bobbink
By Orville M. Kile
PLANT PATENT AGENT Patented Nov. 5, 1935

Plant Pat. 147

UNITED STATES PATENT OFFICE

147

AZALEA

Lambertus Christian Bobbink,
East Rutherford, N. J.

Application June 1, 1935, Serial No. 24,566

1 Claim. (Cl. 47—60)

My invention consists of a distinct improvement in azaleas of the type known as tender or greenhouse evergreen forcing. These new azaleas were produced through a long series of cross breeding involving principally the crossing of the Japanese Kurume azalea with the Indica or Belgian forcing azalea, but involving also the injection of rhododendron blood.

These plant breeding and selecting efforts extending over the past ten years have developed a distinct new type of azalea, differing in many important respects from any of the parent types, and in general combining the large flowers of Indica with the graceful form and floriferousness of the Kurume, but being much more rapid in growth and freer of flowering than either.

I have developed this new type or race of azaleas into three separate and distinct varieties notably differentiated by petal formation and arrangement; namely, single, double, and semi-double, the latter generally known as hose-in-hose.

The subject of my present invention is the "double" variety of this new type of azalea. This variety was produced as follows: First Omursaki was crossed with Mme. Petrick, which produced a double deep wine color flowering in trusses. This in turn was crossed with Rhododendron Mrs. C. S. Sargent. This seemed to improve the quality of the seedlings produced, the best specimen being a large double, deep red in color, flowering in trusses and of vigorous growth habits. This seedling was then crossed with the Indica variety Vervaeneana. This brought forth a double, deep rose in color, flowering in large trusses, having excellent foliage and a graceful form of vigorous growth. With the original variety established, sub-varieties in desired colors are readily secured by well known horticultural methods.

The accompanying illustration shows a typical cluster or truss of flowers fully opened, three typical individual flowers with buds and leaves—all in full color and approximately natural size in the original paintings—and at the upper right a small view in black and white of a small potted plant of this variety.

*The plant.*—Grows rapidly, usually nearly twice as fast as the Indicas and produces salable flowering plants in two years as contrasted with the usual three to four years required for Indica. Some of the sub-varieties of this variety bloom well in advance of the Christmas market while others bloom as late as the end of May, long after Indicas cease blooming.

This variety can be readily grown on its own roots and does not require grafting as is the case with most Belgian Indicas. The rooted plants form an excellent "ball"—so desirable for distant transportation and transplanting.

The form of the plant is bushy but graceful and spreading, forming a solid mass of blossoms when the plant has attained several years growth.

This variety is hardy in the southern tier of States—Georgia, Alabama, Mississippi, South Carolina and similar latitudes.

*Truss formation.*—An important and distinctive feature is the so-called truss structure or formation of the flowering branches. This many-branched structure is similar to that of the American rhododendron. Each branch sends out each year from its terminal bud 3 to 5 or sometimes as many as 7 branches. These branches are relatively short and thus the plant as a whole acquires, after a few years, a very compact and dense growth over its surface area. Each new branch bears at its terminal bud a group of 6 to 12 leaves and 3 to 5 flowers. The result of this peculiar growth habit is that when the large flowers are in bloom the surface and sides of the plant present to the eye a solid mass of color. Each flower crowds its neighbor so closely that very little foliage is visible.

*Foliage.*—Evergreen; the new growth is light green while the old growth, which is the foliage in view when the plants are in bloom, is quite dark green in color.

The individual leaves are small, somewhat spatulate in shape, and of greatly varying lengths in the same cluster, but seldom more than 2 inches long. Taken together, however, the foliage is plentiful and where visible it forms a contrasting background for the blossoms. When not in bloom this rich, dark green foliage provides a pleasing decorative plant. The older leaves drop off gradually during their second year but are constantly replaced by newer leaves.

*Flowers.*—Quite large, measuring in some sub-varieties 3 to 3½ inches across and in nearly all sub-varieties at least 2½ inches. This variety has many petals, usually consisting of two sets of five petals arranged in "hose-in-hose" formation and with extra petals in the middle portion of the flower. These extra petals are attached separately and do not form a tube as is true of the outer petals. Usually there will be five of these extra petals of medium size. But there is considerable variation both as to number and size of these extra petals. These central petals have an infolding formation or arrangement which tends to close up the central portion of the flower and keep the stamens and anthers out of view. Sometimes the style will protrude far enough to penetrate this central arrangement of petals and come into view, but generally no sex-organs in this variety will be visible at a casual glance.

These extra petals, together with their arrangement which prevents ready view of the stamen and style so noticeable in the single and semi-double varieties, give quite a different general appearance to this variety when in full bloom. The edges of the petals are somewhat curled and frilled. One petal in each set of five is heavily flecked with small, dark spots and the adjacent petal on either side of this one petal is slightly flecked.

Stamens are few, long and tipped with prominent anthers. The style usually protrudes beyond the anthers.

The flowers either have been or may be produced, by well known horticultural methods, in all colors and shades ranging from white to dark carmine and including lilac, lavender, mauve and purple, also in combinations of colors.

The flowers remain fresh and beautiful on the plant for an extremely long time—in fact about twice as long as the Indicas which are at present used by florists for forcing. Seven to eight weeks of good bloom are common under ordinary conditions and the period may be lengthened by keeping the plants cool.

Having thus disclosed my invention, I claim:

The variety of evergreen azalea herein described and illustrated characterized particularly by the quick graceful growth and early and profuse flowering of the plant in trusses, by the production of flowers of very large size, of double, many-petalled structure, with sub-varieties blooming over an exceptionally wide range of time and in colors ranging from white to dark carmine.

LAMBERTUS CHRISTIAN BOBBINK.